United States Patent [19]

Schulz et al.

[11] Patent Number: 5,569,752

[45] Date of Patent: Oct. 29, 1996

[54] PROCESS FOR THE PRODUCTION OF LOWER ALKYL OLIGOGLUCOSIDES

[75] Inventors: Paul Schulz, Wuppertal; Herbert Esser, Troisdorf; Rainer Eskuchen, Langenfeld, all of Germany

[73] Assignee: Henkel Kommanditgesellschaft auf Aktien, Duesseldorf, Germany

[21] Appl. No.: 244,647

[22] PCT Filed: Nov. 27, 1992

[86] PCT No.: PCT/EP92/02748

§ 371 Date: Jun. 6, 1994

§ 102(e) Date: Jun. 6, 1994

[87] PCT Pub. No.: WO93/11142

PCT Pub. Date: Jul. 10, 1993

[30] Foreign Application Priority Data

Dec. 6, 1991 [DE] Germany ............... 41 40 334.7

[51] Int. Cl.$^6$ ............... C07H 15/00; C07H 17/00; C07H 1/00; C07G 3/00
[52] U.S. Cl. ............... 536/18.6; 536/18.5; 536/123.1; 536/124; 536/126; 422/135; 422/224
[58] Field of Search ............... 536/18.6, 18.5, 536/123.1, 124, 126; 422/135, 224

[56] References Cited

U.S. PATENT DOCUMENTS

| | | | |
|---|---|---|---|
| 4,223,129 | 9/1980 | Roth et al. | 536/4.1 |
| 4,393,203 | 7/1983 | Mao et al. | 536/124 |
| 4,704,453 | 11/1987 | Lorenz et al. | 536/18.6 |
| 4,713,447 | 12/1987 | Letton | 536/18.6 |
| 4,950,743 | 8/1990 | McCurry, Jr. et al. | 536/18.6 |
| 5,037,992 | 8/1991 | Ward et al. | 558/36 |
| 5,138,046 | 8/1992 | Wuest et al. | 536/18.6 |
| 5,266,690 | 11/1993 | McCurry et al. | 536/18.6 |
| 5,268,461 | 12/1993 | Shoji et al. | 536/4.1 |
| 5,374,716 | 12/1994 | Biermann et al. | 536/18.6 |

FOREIGN PATENT DOCUMENTS

| | | |
|---|---|---|
| 0301298 | 2/1989 | European Pat. Off. |
| 0319616 | 6/1989 | European Pat. Off. |
| 0357969 | 3/1990 | European Pat. Off. |
| 9001489 | 2/1990 | WIPO |

OTHER PUBLICATIONS

Webster's II New Riverside Univ. Dictionary, p. 1175, (1988).

*Primary Examiner*—Ralph J. Gitomer
*Assistant Examiner*—Howard C. Lee
*Attorney, Agent, or Firm*—Wayne C. Jaeschke; John E. Drach; Henry E. Millson, Jr.

[57] ABSTRACT

Light-colored lower alkyl oligoglucosides having a low polyglucose content can be obtained in short reaction times by a process in which a) aqueous glucose sirup is added to a mixture of a lower alcohol and an acidic catalyst at elevated temperatures via an inline mixer, b) the water present in the reaction mixture and the water released are azeotropically distilled off continuously and c) after the addition of glucose sirup, the reaction mixture is subjected to heating until at least 99% of the glucose is reacted.

20 Claims, No Drawings

PROCESS FOR THE PRODUCTION OF LOWER ALKYL OLIGOGLUCOSIDES

BACKGROUND OF THE INVENTION

1. Field of the Invention

This invention relates to a process for the production of lower alkyl oligoglucosides in which glucose sirup is added at elevated temperature to a mixture of a short-chain alcohol and an acidic catalyst via an inline mixer, the water of reaction is azeotropically distilled off and the reaction mixture is subjected to an after-reaction.

2. Statement of Related Art

Surface-active long-chain alkyl oligoglucosides have long been known as raw materials for the production of detergents. They are normally produced by acid-catalyzed acetalization of glucose with long-chain fatty alcohols. In the processes known as the "transacetalization process" or, in special cases, as the "butanol route", the glucose is reacted with a short-chain alcohol, for example butanol, in a first step to form the corresponding glucoside which, in a second step, is subjected to transacetalization with a fatty alcohol. Accordingly, lower alkyl oligoglucosides, such as butyl glucosides for example, are important intermediate products for the production of long-chain alkyl oligoglucosides. In addition, they are directly used as solubilizers and emulsifiers.

European patent application EP 0 319 616 A1 describes a process for the production of lower alkyl oligoglycosides in which an aqueous sugar solution is mixed with a short-chain alcohol, an acidic catalyst is added to the homogeneous solution and the mixture is subsequently reacted at 60° to 200° C. and preferably at 80° to 150° C., any water present being azeotropically distilled off.

International patent application WO 90/1489 describes the reaction of glucose sirups having a DP 1 content (i.e. monomer content) of less than 90% by weight with butanol. The acetalization is carried out with intensive stirring in an aqueous system at temperatures above 125° C. and under pressures of 4 to 10 bar, the reaction mixture being pump-circulated via an inline disperser. The sirup is directly introduced into the reactor. After the addition, the reaction mixture is subjected to an after-reaction to ensure that the glucose is completely reacted off.

The above-mentioned processes have disadvantages which seriously limit their commercial value. If the glucose sirup is introduced into the mixture of alcohol and acidic catalyst too quickly, it is not adequately dispersed, even with intensive stirring. Instead, the glucose sirup passes through a tacky/viscous intermediate stage with release of water, resulting in the formation of agglomerates which are virtually impossible to redisperse. These agglomerates tend to settle mainly on the stirrer unit and cause it to stick and, in extreme cases, to clog up. In addition, another part of the non-dispersed, lumpy starting material usually adheres to the heated reactor wall so that partial carbonization can occur. The acetalization reaction between glucose and alcohol clearly cannot take place optimally where this procedure is adopted. For the most part, the reaction does not take place during the addition, but only during the after-reaction which, for this reason, has to be significantly prolonged.

The problem in question is normally avoided by adding the glucose sirup slowly, i.e. at such a rate that no lumps are formed, instead a single-phase homogeneous system is present or a more or less fine dispersion is formed in which the acetalization can take place without difficulty. Although the after-reaction time can be shortened to an economically acceptable level in this way, the addition time is significantly prolonged so that, in all, long reactor possession times are again the outcome.

Another disadvantage of the long reaction times is that the end reaction products have comparatively high contents of polyglucose and other unwanted secondary products, such as dialkyl ethers for example, and in addition can be seriously discolored by the severe exposure to heat.

Now, the problem addressed by the present invention was to provide an improved process for the production of lower alkyl oligoglucosides which would be free from the disadvantages mentioned above.

DESCRIPTION OF THE INVENTION

The present invention relates to a process for the production of lower alkyl oligoglucosides which is characterized in that a) aqueous glucose sirup is added to a mixture of a lower alcohol and an acidic catalyst at elevated temperatures via an inline mixer, b) the water present in the reaction mixture and the water released are azeotropically distilled off continuously and c) after the addition of glucose sirup, the reaction mixture is subjected to an after-reaction i.e. heating is continued until at least 99% by weight of the glucose has reacted.

It has surprisingly been found that even highly degraded glucose sirup can readily be dispersed in the reaction mixture if it is added via an inline mixer. In this way, the total reaction time, i.e. the sum of the addition time and the after-reaction time, can be significantly shortened. The lower alkyl oligoglucosides obtained are distinguished from the prior-art products by a lighter color and a significantly reduced content of secondary products.

Glucose sirup is understood to be a highly degraded aqueous starch product which has a solids content of 50 to 85% by weight and preferably 70 to 80% by weight, based on the sirup, and a DP 1 value (i.e. a monomeric glucose content) of 90 to 100% by weight, based on the solids content.

Inline mixers which may be used in the process according to the invention are high-speed rotor/stator dispersers in which the shearing elements have a suitably structured surface. Inline mixers particularly suitable for rapid dispersion of the glucose sirup in the reaction mixture have shear rates of $10^4$ to $10^6$ $s^{-1}$. By suitable structuring of the rotor and stator rings, for example by toothing, grooving or perforation, the shear zone is made to pulse as a function of time which intensifies the dispersing effect. Inline mixers which operate with an average shear pulse count per unit volume of $10^5$ to $10^8$ $l^{-1}$ have proved to be optimal.

The inline mixers are preferably incorporated in the liquid circuit outside the reaction vessel. However, the mixing systems may also be operated in a flow guide tube inside the reactor.

Lower alcohols in the context of the process according to the invention are primary alcohols corresponding to formula (I)

$$R^1\text{--OH} \qquad (I)$$

in which

R[1] is a linear or branched alkyl radical containing 3 to 8 carbon atoms. Typical examples are n-propanol, isopropyl alcohol, i-butanol, sec. butanol, tert. butanol, pentanol, hexanol, heptanol, n-octanol and 2-ethyl hexanol. n-Butanol is preferably used.

The acetalization is carried out in the presence of acidic catalysts. Typical examples are methanesulfonic acid, butanesulfonic acid and sulfosuccinic acid. p-Toluenesulfonic acid is preferably used.

To displace the acetalization equilibrium onto the glucoside side, it is advisable initially to introduce the lower alcohol in a considerable excess. Typically, the glucose and lower alcohol may be used in a molar ratio of 1:3 to 1:10 and are preferably used in a molar ratio of 1:6 to 1:8.

The acidic catalyst may be used in a quantity of $3 \cdot 10^{-3}$ to $2 \cdot 10^{-2}$ mol and is preferably used in a quantity of $5 \cdot 10^{-3}$ to $1 \cdot 10^{-2}$ mol per mol glucose.

The alcoholysis of the glucose is preferably a butanolysis. It is advisable in this regard initially to prepare a solution of the acidic catalyst in the excess lower alcohol, to heat the mixture to the reaction temperature of 100° to 115° C. and preferably 108° to 113° C. and continuously to introduce the glucose sirup over a period of 0.1 to 3 and preferably 1 to 2 h at such a rate that a fine-particle dispersion is formed. "Fine-particle" in the present context means that the dispersion is free from clearly visible, tacky agglomerates.

In one embodiment of the process according to the invention, the mixture of glucose sirup, lower alcohol and catalyst is circulated through a falling-film evaporator. The large material transfer surface, the minimal film thickness and the high throughflow rate provide for the particularly gentle transfer of heat and for the highly efficient evaporation of water from the reaction mixture which is reflected in a high color quality of the end reaction products.

To establish the equilibrium, both the water from the glucose sirup and the water of reaction have to be removed as quickly and as completely as possible from the reaction mixture. This is preferably done by means of a standard distillation column through which an azeotropic mixture of water and lower alcohol can be removed. Where butanol is used as the lower alcohol, an azeotrope boiling at around 93° C. is formed and can be distilled off particularly easily.

The alcohol/water mixture removed via the column can be separated in a separation vessel into an upper high-alcohol phase, which is returned to the column, and a lower low-alcohol phase which is separately worked up. This ensures that the process is attended by a minimal loss of lower alcohol.

Addition of the glucose sirup is followed by an after-reaction for about 0.1 to 2 h and preferably for 0.5 to 1.5 h at a temperature of 100° to 115° C., during which it is ensured that all the glucose, i.e. at least 99% by weight, based on the quantity used, has reacted off. The end of the reaction is also signaled by an increase in temperature in the distillation column when only pure lower alcohol rather than the water/alcohol azeotrope is evaporated.

INDUSTRIAL APPLICATIONS

The lower alkyl oligoglucosides produced by the process according to the invention are obtained in short reaction times, have a polyglucose content of less than 2% by weight and preferably less than 1% by weight, based on the solids content of the product, and are distinguished by good color quality.

They are suitable, for example, as intermediate products for the production of relatively long-chain alkyl oligoglucosides for laundry detergents, dishwashing detergents and cleaning products and for hair-care and personal hygiene preparations in which they may be present in quantities of 0.1 to 50% by weight and preferably in quantities of 1 to 25% by weight, based on the particular product.

The following Examples are intended to illustrate the invention without limiting it in any way.

EXAMPLES

Example 1

2,000 g (27 mol) n-butanol and 12.7 g p-toluenesulfonic acid were introduced into a 4-liter stirred reactor and heated to 107° C. under a pressure of 750 mbar. The reaction mixture was pump-circulated through a mixing chamber equipped with a mixer of the Ultra-Turrax® type arranged outside the reactor. 1,160 g glucose sirup (solids content 70% by weight, glucose content 96% by weight, based on solids), corresponding to 4.5 mol glucose, were introduced into the liquid circuit via the mixing chamber of the Ultra-Turrax® over a period of 2 h, a fine dispersion of the glucose in the butanol being formed.

The water of reaction and water which had been introduced with the glucose sirup were distilled off in the form of a butanol/water azeotrope.

The condensate was separated in a separator and the butanol-rich phase was returned to the reactor.

After the addition, the reaction mixture was subjected to an after-reaction for 1 h at 107° C.

The test results are set out in Table 1.

Example 2

870 kg butanol and 4.3 kg p-toluenesulfonic acid were introduced into a 3.2 m³ reactor and heated to 110° C. under a pressure of 950 mbar. A liquid circuit was built up through a pump, an inline mixer (Cavitron® 1039, rotational speed 3100 r.p.m.) and a falling-film evaporator. 470 kg glucose sirup (solids content 70% by weight, glucose content 96% by weight, based on the solids content) were introduced into the inline mixer over a period of 3 h.

The water of reaction and water which had been introduced with the glucose sirup were distilled off in the form of a butanol/water azeotrope.

The condensate was separated in a separator and the butanol-rich phase was returned to the reactor.

After the addition, the reaction mixture was subjected to an after-reaction for 1 h at 110° C. The test results are set out in Table 1.

Comparison Example C1:

The procedure was as in Example 1, except that the glucose sirup was introduced into the reactor directly, rather than through the Ultra-Turrax® over a period of 2h Instead of a fine dispersion, it was found that the glucose sirup had hardly dispersed in the reaction mixture, but instead had settled on the wall of the reactor and particularly on the stirrer. The after-reaction time was increased to 2.5 h. Due to partial carbonization of the glucose sirup on the reactor wall, there were black solid particles in the product. The results are set out in Table 1.

Comparison Example C2:

The procedure was as in Example 2, except that the glucose sirup was introduced into the reactor directly, rather than through the inline mixer, over a period of 2 h. Once again, no fine dispersion was obtained, instead the sirup had settled on the stirrer and the reactor wall. The results are set out in Table 1.

TABLE 1

| | Test results, percentages as % by weight | | | | |
|---|---|---|---|---|---|
| Ex. | t(A) h | t(ARc) h | Dispersion | Product | c(PG) % |
| 1 | 2 | 2 | Fine-particle | Light-colored, clear | <1 |
| 2 | 2 | 1 | Fine-particle | Light-colored, clear | <1 |
| C1 | 2 | 2.5 | Lumpy | Discolored, carbonization | 2.1 |
| C2 | 2 | 3 | Lumpy | Discolored, carbonization | 2.5 |

Legend:
t(A) = Addition time
t(ARc) = After-reaction time
c(PG) = Polyglucose content

What is claimed is:

1. A process for producing a lower alkyl oligoglucoside comprising the steps of:
    (1) adding an aqueous glucose sirup to a heated mixture of a lower alcohol and an acidic catalyst in an inline mixer;
    (2) removing the water of solution and the water of reaction from the resulting mixture by azeotropic distillation with said lower alcohol; and
    (3) heating the mixture following step (2) until at least 99% of the glucose is reacted.

2. The process of claim 1 wherein the solids content of said glucose sirup is from about 70 to about 80% by weight.

3. The process of claim 1 wherein the inline mixer is a high speed rotor/stator disperser.

4. The process of claim 1 wherein the process includes the use of a reaction vessel.

5. The process of claim 4 wherein the inline mixer is positioned outside the reaction vessel.

6. The process of claim 4 wherein the inline mixer is in a flow guide tube inside the reaction vessel.

7. The process of claim 1 wherein the lower alcohol is butanol.

8. The process of claim 1 wherein the shear rate in said inline mixer is from about $10^4$ to about $10^6$ $s^{-1}$; the lower alcohol is a compound of the formula $R^1$—OH wherein $R^1$ is a linear or branched alkyl radical having from 3 to 8 carbon atoms; and the molar ratio of glucose to lower alcohol is from about 1:3 to about 1:10.

9. The process of claim 8 wherein the lower alcohol is butanol.

10. The process of claim 1 wherein the solids content of said glucose sirup is from about 50% to about 85% by weight.

11. The process of claim 1 wherein the monomeric glucose content of said glucose sirup is from about 90% to about 100% by weight of the solids content.

12. The process of claim 1 wherein the shear rate in said in-line mixer is from about $10^4$ to about $10^6$ $s^{-1}$.

13. The process of claim 1 wherein the average shear pulse count per unit volume in said in-line mixer is from about $10^5$ to about $10^8$ $s^{-1}$.

14. The process of claim 1 wherein said lower alcohol is a compound of the formula I $$R^1\text{—OH} \qquad (I)$$

wherein $R^1$ is a linear or branched alkyl radical having from 3 to 8 carbon atoms.

15. The process of claim 1 wherein said acid catalyst is p-toluenesulfonic acid, methanesulfonic acid, butanesulfonic acid, or sulfosuccinic acid.

16. The process of claim 1 wherein the molar ratio of glucose to lower alcohol is from about 1:3 to about 1:10.

17. The process of claim 16 wherein said molar ratio is from about 1:6 to about 1:8.

18. The process of claim 1 wherein the molar ratio of acid catalyst to glucose is from about $3\times10^{-3}$:1 to about $2\times10^{-2}$:1.

19. The process of claim 1 wherein in step (1) said mixture is comprised of a fine particle dispersion formed by adding said glucose to a solution of said acid catalyst in said lower alcohol over a period of from about 0.1 hours to about 3 hours at a rate sufficient to form fine particles.

20. The process of claim 1 wherein step (3) is carried out at a temperature of from about 100° C. to about 115° C.

* * * * *